US005510460A

United States Patent [19]

Hayward

[11] Patent Number: 5,510,460

[45] Date of Patent: Apr. 23, 1996

[54] PEPTIDE PROCESS

[75] Inventor: Christopher F. Hayward, Macclesfield, England

[73] Assignee: Zeneca Limited, London, United Kingdom

[21] Appl. No.: 451,980

[22] Filed: May 26, 1995

Related U.S. Application Data

[63] Continuation of Ser. No. 199,015, Feb. 18, 1994, abandoned, which is a continuation of Ser. No. 897,496, Jun. 12, 1992, abandoned.

[30] Foreign Application Priority Data

Jun. 14, 1991 [GB] United Kingdom .................. 9112859

[51] Int. Cl.$^6$ ................................ C07K 7/23; C07K 7/06

[52] U.S. Cl. ......................... 530/328; 530/313; 530/334; 530/345

[58] Field of Search .................................... 530/334, 328, 530/345, 313

[56] References Cited

U.S. PATENT DOCUMENTS 4,100,274 7/1978 Dutta et al. ............................ 424/177

OTHER PUBLICATIONS

Dutta et al. J.C.S. Perkin I (1975) 1712–1720.

Folkers et al. Z. Natur. B: Anorg. Chem. Org. Chem. 37B (8), 1075–1081 (1982).

Folkers et al.; "Synthesis and Bioassay of Antagonists of the Luteinizing Hormone Releasing Hormone Having The Aza-gly–10 Moiety; Zeitschrift fur Naturforschung" p. 1076, Col. 1–2 (Aug. 1982).

Dutta et al.; "Polypeptides, Part X111. Preparation of Alpha–Aza–Amino Acid (Carbazic Acid) Derivatives and Intermediates for the Preparation of Alpha–Aza–Peptides"; Journal of the Chemical Society; pp. 1712–1720 (1975).

Cotton et al.; "The Synthesis of [D–Ser(But)–6,Azgly–10] LHRH (Zoladex–R*) By Solid–Phase Procedures Twelfth American Peptide Symposium", Mass. Inst. of Technology, Cambridge, Program and Abstracts, p. 412 (Jun. 1991).

Knolle et al., Solid phase synthesis of glycosylated LHRH antagonists with C–terminal azaglycine–amide, Peptides, pp. 414–415, 1990.

*Primary Examiner*—Howard E. Schain
*Attorney, Agent, or Firm*—Cushman Darby & Cushman

[57] ABSTRACT

A process for the solid phase synthesis of peptides containing an aza-amino acid, for example the decapeptide goserelin, which comprises:

(i) assembling all the amino acids of the peptide except the C-terminal aza-amino acid by conventional solid phase synthesis;

(ii) cleaving the peptide from the support with hydrazine or a substituted hydrazine; and (iii) reacting the hydrazide thus released with a cyanate ion.

1 Claim, No Drawings

PEPTIDE PROCESS

This is a continuation of U.S. Ser. No. 08/199,015, filed Feb. 18, 1994, now abandoned, which is a continuation of application Ser. No. 07/897,496 , filed on Jun. 12, 1992, which was abandoned upon the filing hereof.

This invention relates to a process for making peptides and more particularly it relates to a solid phase peptide synthesis method for the preparation, inter alia, of the decapeptide goserelin.

The solid phase synthesis of peptides has been known for almost 30 years following the pioneering work of Merrifield first published in 1962. The general principle of this type of synthesis is as follows:

(a) An N-protected amino acid (the protecting group is commonly t-butoxycarbonyl, abbreviated to Boc) is attached to a solid, non-soluble support (commonly a polystyrene resin) at its carboxylic end via a linking group (commonly a benzyl ester).

(b) The N-protecting group is removed by means which do not detach the amino acid from the solid support, and a second N-protected amino acid is coupled to the one already attached (commonly by use of a carbodiimide coupling agent).

(c) The sequence is repeated using as many N-protected amino acids as are required until the desired peptide has been formed, still attached at its carboxyl end to the solid support.

(d) The final N-protecting group is removed and the peptide is separated from the solid support by cleavage of the linking group (commonly by use of a strong acid).

The whole synthesis can be machine-aided and in some circumstances the peptide may be formed without manual intervention. The Boc protecting groups are removed by trifluoroacetic acid and the peptide chain is removed from the solid support with a stronger acid such as hydrofluoric acid.

Since the introduction of this technique many modifications have been introduced, but the process generally used today is essentially as first described. Two major innovations have been the use of a polyamide as the solid support and the use of a N-fluoren-9-ylmethoxycarbonyl (Fmoc) protecting group for the $N^{\alpha}$-group of the amino acid. The Fmoc group is distinguished by being labile to base (commonly piperidine). For further detail reference is made, for example, to Atherton and Sheppard, "Solid phase peptide synthesis—a practical. approach", IRL Press at Oxford University Press, 1989; Barany et al., "Solid-phase peptide synthesis: a silver anniversary report", Int. J. Peptide Protein Res., 1987, 30, 705–739 and Fields et al., ibid, 1990, 35, 161–214.

Throughout this specification standard abbreviations for amino acids, protecting groups, coupling agents and the like will be used. For the avoidance of doubt, as well as Boc and Fmoc defined above, the following are relevant standard abbreviations:

| | |
|---|---|
| Arg | arginine |
| Azgly | azaglycine ($H_2N$—NH—COOH) |
| D-Ser | D-serine |
| Glp | pyroglutamic acid |
| His | histidine |
| Leu | leucine |
| Pro | proline |
| Ser | serine |
| Trp | tryptophan |

-continued

| | |
|---|---|
| Tyr | tyrosine |
| DIPC | di-isopropylcarbodi-imide |
| HOBt | 1-hydroxybenzotriazole |
| DMF | N,N-dimethylformamide |
| BrZ | 2-bromobenzyloxycarbonyl |
| $Bu^t$ | tert-butyl |
| Bzl | benzyl |

Goserelin is an LHRH analogue used in the treatment of prostate cancer, breast cancer and certain gynaecological conditions. In the first-mentioned treatment it acts by inducing a chemical castration. Its structure is:

Glp—His—Trp—Ser—Tyr—D—Ser($Bu^t$)—Leu—Arg—Pro—Azgly—$NH_2$

It will be seen that there are two features of this structure which are incompatible with traditional solid phase peptide synthetic routes. The first is the Azgly carboxy terminal amino acid; procedures for linking such a group to a solid support are not known, although Knolle et al., Peptides 1990, 414–415, describe attaching the dipeptide Pro-Azgly to an aminomethyl resin through a substituted phenylpropionic acid linking group. Free azaglycine, of course, has a terminal —NH—COOH group, which is an unstable carbamic acid.

The second feature of goserelin which is incompatible with traditional solid phase synthesis is the tert-butyl group attached to the D-serine moeity; in order to preserve this group traditional means for removing the completed peptide from the solid support by the use of strong acid cannot be used.

The present invention provides a process for the manufacture of goserelin and other peptides containing C-terminal aza-amino acids by solid phase synthesis.

According to the invention there is provided a process for solid phase synthesis of a peptide containing a C-terminal aza-amino acid amide which comprises:

(i) assembling all the amino acids of the peptide except the C-terminal aza-amino acid by conventional solid phase synthesis;

(ii) cleaving the peptide from the support with hydrazine or a substituted hydrazine; and (iii) reacting the hydrazide thus released with a cyanate ion.

The last two stages of this process form firstly a peptide having a carboxyl end of the formula:

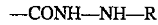

—CONH—NH—R wherein R is hydrogen (in Azgly) or such a group that $H_2N$—NR—COOH is an aza-analogue of an amino acid, and secondly a peptide with the carboxyl end of the formula:

—CONH—NR—$CONH_2$

The cleavage of the peptide from the support may be carried out using hydrazine or a substituted hydrazine in solution in DMF, N-methylpyrrolidone or a similar solvent.

A suitable cyanate ion may be provided by an alkali metal cyanate, for example potassium or sodium cyanate. The reaction may be carried out in aqueous acidic conditions.

According to a further feature of the invention there is provided a method for solid phase synthesis of a peptide containing an amino acid which contains a tert-butyloxy group in its side chain, which comprises the use of a linking group, connecting the amino acid to the solid support, which is labile under conditions which do not cleave an O-tert-butyl group.

A suitable linking group is one which may be cleaved by the use of hydrazine which will not cleave the tert-butyl ether, for example the benzyl ester. Suitable conditions which will remove the peptide from the resin without also removing the tert-butyl group on the side chain are, for example, the use of hydrazine.

Amino acids which Contain a tert-butyloxy group in the side chain are, for example, serine, D-serine, threonine, tyrosine and hydroxyproline.

More particularly, the invention provides a process for solid phase synthesis of goserelin which comprises:

(i) assembling all the amino acids of goserelin except the C-terminal aza-glycine by conventional solid phase synthesis;

(ii) cleaving the peptide from the support with hydrazine or a substituted hydrazine; and (iii) reacting the hydrazide thus released with a cyanate ion to form goserelin.

The invention is illustrated but not limited by the following example:

EXAMPLE (a) Solid Phase Preparation of Nonapeptide

The solid phase synthesis was carried out in automatic mode on an Applied Biosystems 430A Peptide Synthesizer using Boc-Pro-OBzl-polystyrene resin 1% cross-linked with divinylbenzene (Peninsula Laboratories, 1.25 g, 0.38 meq/g though nominally 0.7 meq/g). The following protected amino acids were converted to benzotriazolyl esters by reaction with HOBt and DIPC in DMF immediately before use. The protected amino acids were coupled in the following sequence:

Boc—Arg(HCl)—OH

Boc—Leu—OH

Fmoc—DSer(But)—OH

Fmoc—Tyr(BrZ)—OH

Fmoc—Ser—OH

Fmoc—Trp—OH

Fmoc—His(Fmoc)—OH

Pyr—OH

The sequence of operations for the first two stages (using Boc-protected-amino acids) was:

removal of Boc with 45% triflouroacetic acid in dichloromethane;

10% DIEA/DMF wash;

coupling (2 equivalents of protected amino acid HOBt ester);

removal of Boc as above.

The sequence of operations for the last six stages (using Fmoc-protected-amino acids) was:

removal of Fmoc with 20% piperidine/DMF;

0.5 molar HOBt/DMF wash;

coupling (1 equivalent of protected amino acid HOBt ester).

All coupling reactions except that using Boc—Arg(HCl)—OH were of 1 hour duration; the Boc—Arg(HCl)—OH one was of 2 hours duration. There was thus obtained the nonapeptide-resin (1.7g; 0.29 mmole peptide per g.) with the Tyr still protected by BrZ.

(b) Cleavage of Peptide From Resin

The peptide resin prepared above was treated with a 20-fold excess of anhydrous hydrazine in DMF (20 ml) at laboratory temperature for 24 hours, and the mixture was filtered and evaporated to dryness. This procedure also removed the BrZ protecting group from the Tyr moeity. The residue was purified by gel filtration on a column (LH 20 Sephadex) using a 20:1 v/v mixture of water and acetic acid as eluant. There was thus obtained

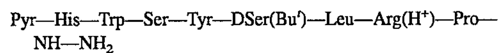

the structure of which was confirmed by amino acid analysis and FAB mass spectroscopy $(M+H)^+=1226$.

(c) Preparation of Goserelin

A solution of potassium cyanate (11 mg) in water (1.36 ml) was added portionwise during 1 hour to a solution of the above hydrazide (118 mg) in a 20:1 v/v mixture of water and acetic acid (10 ml). The mixture was freeze-dried and the residue was purified by reverse-phase column chromatography (Dynamax 60 Å, $C_{18}$, 1 inch diameter) using a gradient of 10% to 40% by volume of acetonitrile in water containing 0.1% trifluoroacetic acid. There was thus obtained goserelin (100 mg, 25% yield overall), the structure of which was confirmed by FAB mass spectroscopy, giving a characteristic mass ion at 1269.

I claim:

1. A process for solid phase synthesis of goserelin which comprises:

(i) synthesizing all the amino acids of goserelin except the C-terminal aza-glycine by conventional solid phase synthesis;

(ii) cleaving the peptide from the support with hydrazine or a substituted hydrazine; and (iii) reacting the hydrazide thus released with a cyanate ion to form goserelin.

* * * * *